United States Patent [19]
Shiber

[11] Patent Number: 5,195,540
[45] Date of Patent: Mar. 23, 1993

[54] LESION MARKING PROCESS

[76] Inventor: Samuel Shiber, P.O. Box 1366, Atkinson, N.H. 03811

[21] Appl. No.: 744,462

[22] Filed: Aug. 12, 1991

[51] Int. Cl.$^5$ ............................................. A61B 17/34
[52] U.S. Cl. ..................................... 128/898; 606/185
[58] Field of Search ...................... 606/185, 116, 129; 604/264; 128/898, 751–754

[56] References Cited

U.S. PATENT DOCUMENTS

| | | | |
|---|---|---|---|
| 4,592,356 | 6/1986 | Gutierrez | 606/185 |
| 4,931,059 | 6/1990 | Markham | 606/185 |
| 5,059,197 | 10/1991 | Urie et al. | 606/116 |

Primary Examiner—Michael H. Thaler
Attorney, Agent, or Firm—Samuel Shiber

[57] ABSTRACT

A lesion marking system comprising a guiding needle rotatably and slidably supporting a spiral wire which is cork screwed, under an imaging system guidance, into a lesion. The guiding needle is then withdrawn, leaving the spiral wire as a visible lesion marker.

2 Claims, 1 Drawing Sheet

LESION MARKING PROCESS

With age, a percentage of the population develops lesions, for example, cysts and tumors. These lesions are commonly diagnosed by a radiologist who uses imaging systems such as X-rays and ultrasound systems. It is often helpful to mark these lesions during the diagnostic procedure so that a surgeon can visually locate and excise the lesion during a subsequent surgery.

An objective of the present invention is to provide a lesion marking system that can be visualized, during the diagnostic procedure, through the imaging system, as well as by the naked eye for subsequent continued treatment. A further objective is to provide a system which will not, inadvertently, drift and move relative to the lesion. Another objective is to reduce the trauma caused to the patient by the marking process by minimizing the puncture wound created by the placement of the system.

The system comprises a relatively thin guide needle which is inserted to the lesion under guidance of the imaging system. Once the needle is in place, a spiral wire is cork-screwed around the needle to the lesion. Then, the needle may be withdrawn leaving the spiral wire in place as a marker. The spiral wire by itself is flexible and its proximal section which is left sticking out of the patient's body can be bent and taped to the patient to prevent the spiral wire from unscrewing and drifting relative to the lesion and to reduce the discomfort to the patient.

The above and other objectives of the invention will become apparent from the following discussion and the accompanying drawings.

DETAILED DESCRIPTION OF THE DRAWINGS

A lesion marking system 10 comprises elongated parts in a nested relationship. Their ends shall be referred to as "distal" meaning the end which enters the patient's body first, and "proximal" meaning the other end.

Figure 2:
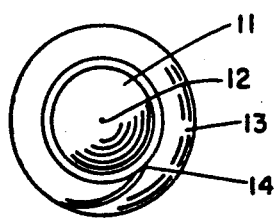
FIG. 2 shows an enlarged end view of the lesion marking system as viewed from line 2—2, marked on FIG. 1.
Figure 1:
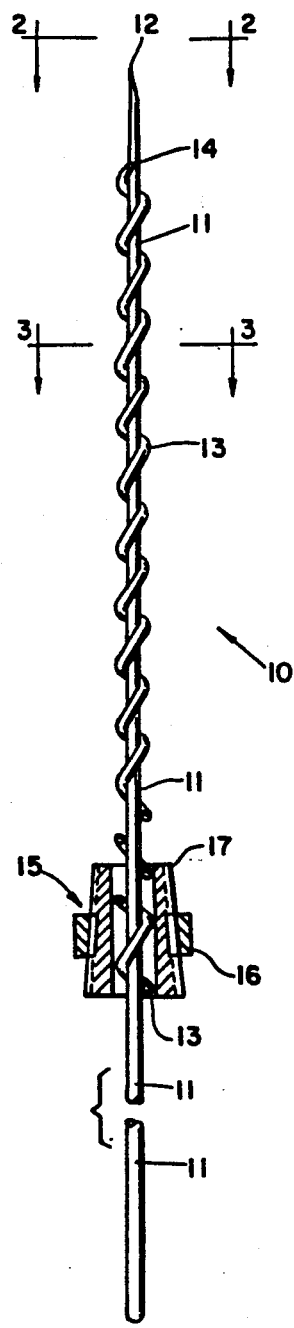
FIG. 1 shows a partially sectioned side view of a lesion marking system according the present invention.
Figure 3:
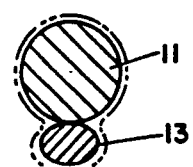
FIG. 3 shows an enlarged cross sectional view of the lesion marking system as viewed along line 3—3, marked on FIG. 1. The periphery of a skin puncture wound needed to introduce the system into the body, is shown in a phantom line.

FIG. 1 shows the lesion marking system 10 which comprises:

A guiding needle 11 having a sharp distal tip 12.

A spiral wire 13 which is rotatably and slidably supported on the guiding needle. The spiral wire has a sharp distal tip 14 and a removeable handle 15 at its proximal section. The handle can be affixed to the spiral wire by tightening a nut portion thereof 16 onto the externally threaded conical body portion thereof 17 (such handles are commercially available for medical and for industrial applications and operate similarly to a miniature drill chuck).

The guiding needle and the spiral wire can be made from stainless steel.

To enhance their radio-opacity, especially in small size versions of the system, at least the distal part of the guiding needle and spiral wire can be plated with materials such as gold or platinum. Alternatively, the guiding needle and the spiral wire can be made from materials that are easily visualized by imaging systems.

OPERATION

Figure 4:
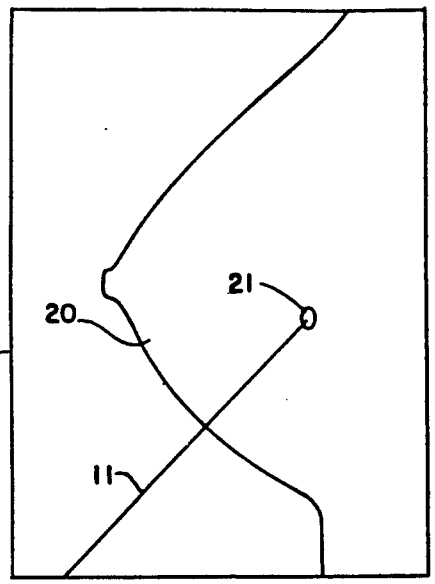
FIG. 4 shows a guiding needle inserted to a lesion in a mammary gland of a patient, as viewed on a display of an imaging system.
Figure 5:
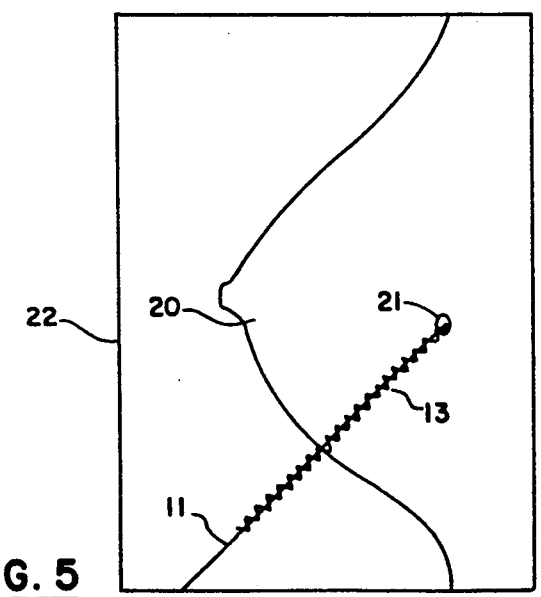
FIG. 5 shows a spiral wire which has been slid and rotated (cork-screwed) over the guiding needle, to the lesion, as viewed on a display of an imaging system.
Figure 6:
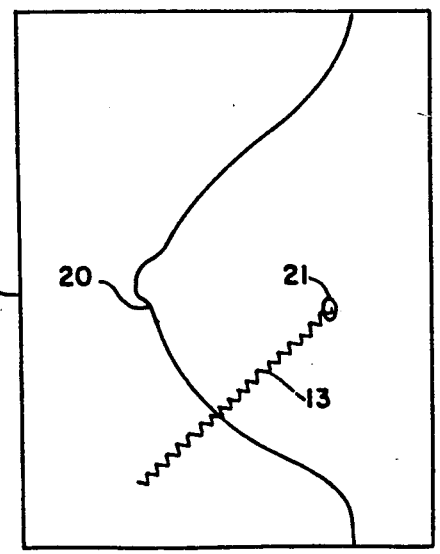
FIG. 6 shows the spiral wire marking the lesion after the guiding needle was withdrawn from the mammary gland, as viewed on a display of an imaging system.

The process of marking a lesion is illustrated in FIGS. 4, 5 and 6, and comprises the following steps:

FIG. 4 illustrates the guiding needle inserted to a lesion 21 in a patient's mammary gland 20, as viewed on the a display 22 of an imaging system. Since both the lesion and the components of the lesion marking system are visible on the a display 22, the radiologist can accurately direct the needle to the lesion. A biplane imaging system is preferable to assure that the needle is not placed below or above the lesion.

FIG. 5 illustrates the spiral wire, that has been slid and rotated over the guiding needle like a cork screw, to the lesion site, as viewed on the display 22.

FIG. 6 illustrates the spiral wire, as viewed on the display 22, after the guiding needle was withdrawn from the mammary gland the spiral wire is left in place to mark the lesion 21. The proximal section of the spiral wire which is left sticking out of the patient's body can be bent and taped to the patient's body, to prevent it from unscrewing and drifting from the lesion and to reduce discomfort to the patient. Since the spiral wire is also visible to the naked eye it serves to readily locate the lesion later on, for example during surgery.

A hollow (hypodermic) guiding needle can be used to allow the radilogist to extract tissue samples (biopsy) and to inject a dye to augment the mechanical marking by the spiral wire with tissue staining of the area of the lesion.

The spiral wire can be cork screwed manually or the handle 15 can be coupled to a motor drive of the type shown, for example, in my U.S. Pat. No. 5,002,553, for driving the spiral wire to the lesion.

While the present invention has been illustrated by a single embodiment, it should be understood the above and other modifications and substitutions may be made without departing from the spirit of the invention or the scope of the claims.

I claim:

1. A lesion marking process comprising the following steps:
   Inserting a guiding needle to the vicinity of the lesion while using an imaging system for guidance,
   rotating and sliding a spiral wire over the guiding needle to the vicinity of the lesion while using an imaging system for guidance,
   withdrawing the guiding needle from the patient, leaving the spiral wire in the vicinity of the lesion as a marker.

2. A lesion marking process as in claim 1, an additional step wherein a dye is introduced through the guiding needle to stain the lesion.

* * * * *